(12) United States Patent
Henderson et al.

(10) Patent No.: US 7,960,686 B2
(45) Date of Patent: Jun. 14, 2011

(54) RADIOGRAPHIC CALIBRATION APPARATUS

(75) Inventors: Jarrid L. Henderson, Pittsburgh, PA (US); Jeremy B. Hoover, Meyersdale, PA (US)

(73) Assignee: J2 Medical, LP, Pittsburgh, PA (US)

( * ) Notice: Subject to any disclaimer, the term of this patent is extended or adjusted under 35 U.S.C. 154(b) by 141 days.

(21) Appl. No.: 12/108,121

(22) Filed: Apr. 23, 2008

(65) Prior Publication Data

US 2008/0292063 A1 Nov. 27, 2008

Related U.S. Application Data (60) Provisional application No. 60/925,547, filed on Apr. 23, 2007.

(51) Int. Cl.
*G01D 18/00* (2006.01)
*H05G 1/00* (2006.01)
(52) U.S. Cl. ............... 250/252.1; 378/207; 378/208; 356/401
(58) Field of Classification Search .............. 250/252.1, 250/202; 378/207, 208, 163; 356/401, 402
See application file for complete search history.

(56) References Cited

U.S. PATENT DOCUMENTS

| | | | |
|---|---|---|---|
| 5,142,930 A * | 9/1992 | Allen et al. ................... 74/469 |
| 5,149,965 A * | 9/1992 | Marks ........................ 250/252.1 |
| 5,216,700 A * | 6/1993 | Cherian ........................ 378/163 |
| 5,394,457 A * | 2/1995 | Leibinger et al. ............. 378/162 |
| 5,730,130 A * | 3/1998 | Fitzpatrick et al. ........... 600/407 |
| 7,500,570 B2 | 3/2009 | Kurcheski |
| 2002/0085197 A1* | 7/2002 | Slocum et al. ................ 356/220 |

OTHER PUBLICATIONS

Orthomark product image available at http://www.orthomark.net/images/OM1.gif, 1 page.
Image and description of a Flex Stand offered for sale at http://www.xemarc.com/ProductDetails.asp!ProductCode=STA%2D25B, 1 page.

* cited by examiner

*Primary Examiner* — David P Porta
*Assistant Examiner* — Jessica L Eley
(74) *Attorney, Agent, or Firm* — IN-IP Law Group, P.C.

(57) ABSTRACT

A radiographic calibration apparatus for supporting a calibration unit. The radiographic calibration apparatus includes a support structure, and this support structure or arrangement is used to support and selectively position the calibration unit with respect to a patient. A retaining member for use in connection with a calibration unit is also disclosed.

17 Claims, 6 Drawing Sheets

RADIOGRAPHIC CALIBRATION APPARATUS

CROSS REFERENCE TO RELATED APPLICATION

This application claims the benefit of priority of U.S. Provisional Patent Application Ser. No. 60/925,547, filed Apr. 23, 2007, which is incorporated herein by reference in its entirety.

BACKGROUND OF THE INVENTION

1. Field of the Invention

The present invention relates generally to radiography and related calibration apparatuses and, more particularly, to a calibration apparatus that allows for efficient securing in an area of interest for positioning a calibration unit near a radiography target.

2. Description of Related Art

Many procedures in the medical field and otherwise use radiography to produce images for assessing radiopaque materials. One example is the use of radiography in taking orthopedic x-rays. An x-ray image must be calibrated in order to appropriately scale the joint and bone structure of the patient. Currently, for example, a 25.4 millimeter (approximately 1 inch) metal sphere is employed and placed near the area of interest in order for it to show up in the x-ray, for use in calibrating the image to scale using the known dimensions of the metal sphere.

Problems often arise when attempting to keep the metal ball in place during the x-ray process. Patients often lie on a horizontal or vertical table throughout the duration of the x-ray so options are limited for placement of the metallic ball without additional securing assistance.

According to the prior art, one solution currently on the market is an adhesive strip that is applied directly to the skin of the patient, regardless of the location, and the calibration sphere is then stuck to the back side of the strip. One problem with an adhesive strip is that it is generally uncomfortable for both the patient and the technologist to physically place the strip onto the body of the patient. This is particularly problematic where the skin of the patient has sores or is prone to tearing of the patient's skin upon removal. Another issue that commonly arises is that the body hair of the patient can be too intense for the strip to properly adhere given the weight of the calibration sphere.

Further, where the calibration sphere is taped near a radiographic target in a vertical position such as, for example, a patient's knee, while standing upright the strip may not be able to support the weight of the calibration sphere. In addition, the strip is uncomfortable and sometimes painful, or possibly damaging to the skin when removed upon completion of the x-ray. Many times the strip must be placed in a private area of the patient. Still further, the strips are disposable, creating a recurring expense for the owner and higher prices are then passed along to the patient or radiography facility.

SUMMARY OF THE INVENTION

Accordingly, it is one object of the present invention to provide a radiographic calibration apparatus that overcomes many of the drawbacks and deficiencies of the prior art systems and arrangements. It is another object of the present invention to provide a radiographic calibration apparatus that permits selective positioning of a calibration unit with respect to a patient.

In accordance with the present invention, provided is a radiographic calibration apparatus for supporting a calibration unit. The radiographic calibration apparatus includes a support structure, and this support structure or arrangement is used to support and selectively position the calibration unit with respect to a patient. In one preferred and non-limiting embodiment, the support structure of the radiographic calibration apparatus includes a radiolucent extension for supporting the calibration unit, as well as a selectively positionable arm. The positionable arm may be supported by a base that is configured to stabilize the calibration unit in a desired position and orientation.

In accordance with another aspect of the present invention, provided is a retaining member for supporting a calibration unit in a radiographic calibration apparatus wherein the retaining member has at least two leaf portions. The at least two leaf portions may be configured to at least partially surround and support at least a portion of the calibration unit and have some resilient properties. Each of the at least two leaf portions has a receiving surface configured to deflect the at least two leaf portions when the calibration unit is urged into contact with the receiving surface. Each of the at least two leaf portions has a retaining surface configured to at least partially surround and engage or support at least a portion of the calibration unit.

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and the claims, the singular form of "a", "an", and "the" include plural referents unless the context clearly dictates otherwise.

DESCRIPTION OF THE PREFERRED EMBODIMENT(S)

For purposes of the description hereinafter, the terms "upper", "lower", "right", "left", "vertical", "horizontal", "top", "bottom", "lateral", "longitudinal" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

The present invention is directed to a radiographic calibration apparatus ("RCA") 1, which is illustrated in various preferred and non-limiting embodiments in FIGS. 1-6. The RCA includes a support structure 3 for supporting and selectively positioning (or orienting) a calibration unit 90 with respect to a patient to be x-rayed. As discussed hereinafter, this support structure 3 may take a variety of forms for providing the unique ability to selectively position and orient the calibration unit 90 to a desired location and position with respect to the patient.

Figure 1:
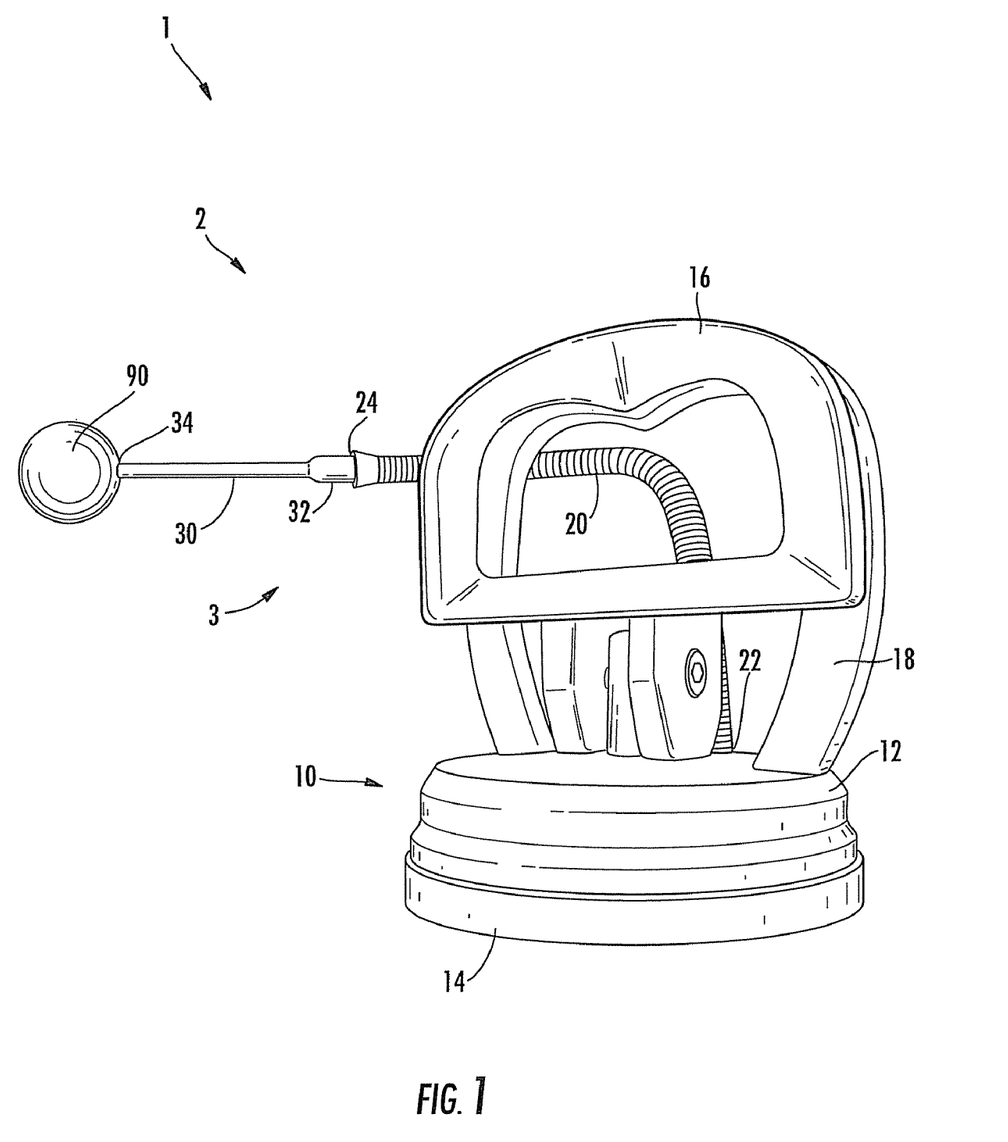
FIG. 1 is a perspective view of one embodiment of a radiographic calibration apparatus supporting a calibration unit in accordance with the present invention.

One preferred and non-limiting embodiment of an RCA 2 according to the present invention is illustrated in FIG. 1. In this embodiment, the support structure 3 of the RCA 2 includes an extension 30 for supporting the calibration unit 90. Further, the support structure 3 of the RCA 2 includes a base 10 and an arm 20. The extension 30 supports the calibration unit 90 and allows for the selective positioning of the calibration unit 90 in an area of interest near a radiography target such as, for example, the femoral bone of a patient being x-rayed.

As can be seen in FIGS. 1-4, the base 10, may be a suction hand cup 12 that is manually operated for securing generally to substantially non-porous materials. Generally, the suction hand cup 12 may have an elastic pad 14 that is removably securable to a generally non-porous surface through the operation of a cam lever 16 toward a lever grip 18. Thus, the pad 14 may be pressed onto a clean, dry, generally non-porous surface to which the RCA 2 will be secured with the cam lever 16 in a spaced positioned from the lever grip 18. While the pad 14 is pressed against a securing surface (e.g. x-ray table, window, etc.), the lever grip 18 may be grasped and the cam lever 16 squeezed toward the lever grip 18 and moved into position next to the lever grip 18. Accordingly, the pad 14 may be securely attached to a securing surface by the vacuum formed when the cam lever 16 is positioned adjacent the lever grip 18. In order to release the suction hand cup 12, a user would reposition or actuate the cam lever 16 away from the lever grip 18. It should be noted that the base 10 may be made from any suitable securing device (e.g. clamp, suction cup, attaching structure, etc.) that serves to removably secure the RCA 2 to either a vertical or horizontal surface next to a patient that may be exposed to some radiographic procedure including, for example, x-ray.

In one preferred and non-limiting embodiment, the arm 20 is selectively repositionable, as illustrated in the exemplary embodiments of FIGS. 1-4 and 6. Accordingly, the arm 20 may be flexible or otherwise movable and/or maneuverable in relation to the base 10 and can be maneuvered into a variety of positions, as shown in FIG. 1. The arm 20 may have a first end 22 in communication with the base 10 and a second end 24 in communication with the extension 30. In the embodiment illustrated in FIG. 1, the arm 20 may be secured to the base 10 via threaded engagement, injection molded, press fit, removable attachment, integral attachment, etc., as determined for a given application.

Arm 20 may or may not be radiolucent depending upon the given application for which the RCA 2 will be employed. Thus, arm 20 may be comprised of various flexible, deformable and/or repositionable structures, such as, for example, metallic flexible conduit, interlinked polymeric elements, etc. In addition, where sanitary environments necessitate sterile surfaces or a minimization of possibility for contamination, the arm 20 may be polymeric coated or otherwise provided with antimicrobial properties.

As can be seen in FIG. 1, the second end 24 of the arm 20 may be in operative communication with extension 30 at a proximal end 32 to the arm 20, e.g., the second end 24 of the arm 20. Accordingly, the extension 30 is in direct or indirect operative communication with and supports the calibration unit 90 at a distal end 34 of the extension 30. The extension 30 may be integrally formed with or directly or indirectly attached to the arm 20. Further, and as will be determined by the given application, the extension 30 may be affixed or otherwise secured to the calibration unit 90 via threaded engagement, press fit, etc. Extension 30 may be radiolucent, such that the dimensions of the calibration unit 90 may not be obfuscated in any way on the radiographic image to be taken.

In addition, and in a preferred and non-limiting embodiment, the extension 30 may incorporate an optional radiopaque indicia or portion (not shown) that will show up in the x-ray in order to show the size of the calibration unit 90 being used. For example, this radiopaque indicia or portion may take the form of lead or other radiopaque indicia to indicate the precise dimension of the calibration unit 90 on the radiographic image. Such radiopaque indicia or portions may further prevent errors made by a technologist otherwise manually transcribing the dimensions of the calibration unit 90 onto the radiographic image (e.g. x-ray image).

Although the calibration unit 90 may be positioned at any point on the support structure, in the embodiment of FIG. 1, the calibration unit 90 is supported by the extension 30, and specifically at the distal end 34 of the extension 30. Accordingly, the support structure 3 of the RCA 2 supports the calibration unit 90 via the extension 30, such that the calibration unit 90 will be positioned away from any conflicting radiopaque materials that may be present in the base 10 or arm 20, wherein the extension 30 is made of a radiolucent material. Thus, the extension 30 made of a radiolucent material may hold the calibration unit 90 away from the arm 20, wherein the arm 20 may be formed of a radiopaque material, to ensure unwanted radiopaque images do not interfere with the area of interest for the radiography target.

As can be seen in the embodiment shown in FIG. 1, the calibration unit 90 may be permanently affixed or removably secured to the extension 30. The calibration unit 90 may thus be shaped or otherwise configured in the present embodiment to be engageable with the extension 30. Any effective manner of attaching, coupling or otherwise engaging the calibration unit 90 with the extension 30 (or any portion of component of the support structure 3) is envisioned.

Further, in one preferred and non-limiting embodiment, the calibration unit 90 is formed of a radiopaque material such as, for example, a metallic material, such that the precise dimensions of the calibration unit 90 may be observed in the area of interest of the radiography target. Thus, the calibration unit 90 is preferably a precise spherical dimension such that regardless of the angle of the radiograph taken, the dimensions of the calibration unit 90 will be consistent. Accordingly, the calibration unit 90 may be, for example, precisely 25.4 millimeter (1 inch) in diameter, such that when the radiographic image is taken past the radiopaque calibration unit 90, the size of surrounding radiopaque materials (e.g. bone mass) will be known in scale to the calibration unit 90. Variously sized and shaped calibration units 90 formed of radiopaque materials with precise known measurements may also be employed, including, for example, a coin, ball bearing, BB, etc. as may be commonly used in a given radiographic facility.

In one embodiment, the calibration unit 90 may be positioned within an area of interest next to a radiograph target. As mentioned above, in one embodiment, the calibration unit 90 has the advantage of having a precise circular image projected, regardless of the position of the radiographic equipment relative to the calibration unit 90. Further, some radiographic equipment may have zooming features as in, for example, a regular digital camera such that different radiographic targets (e.g. bones) may not appear the same size in the final images. Thus, through the ability to position the calibration unit 90 in multiple desired orientations next to the radiographic target, the size of the radiographic target may be known by referencing the scale to the calibration unit 90, regardless of what zoom level is used, or at what angle the image is taken.

Figure 2:
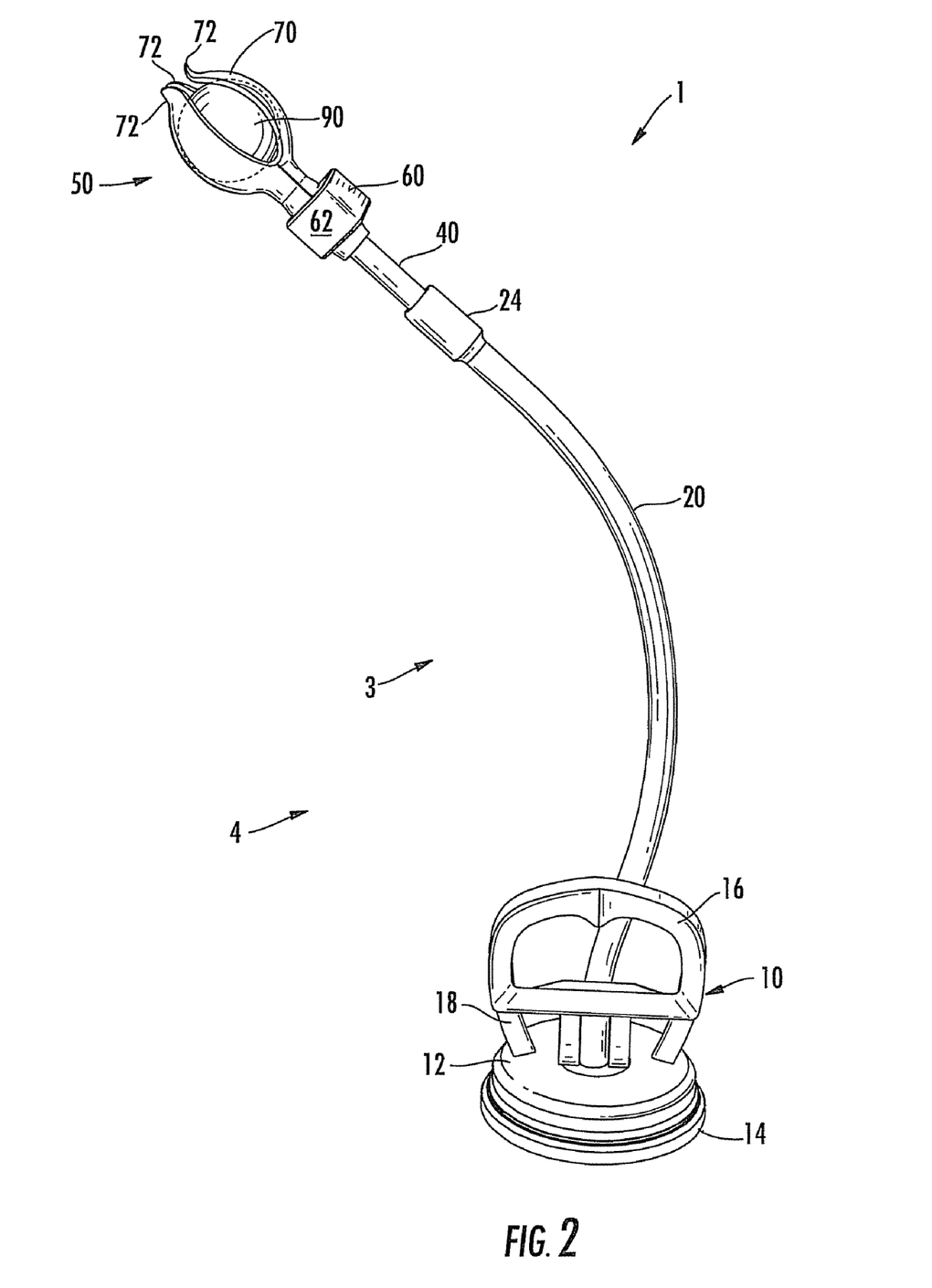
FIG. 2 is a perspective view of another embodiment of a radiographic calibration apparatus supporting a calibration unit in accordance with the present invention.
Figure 3:
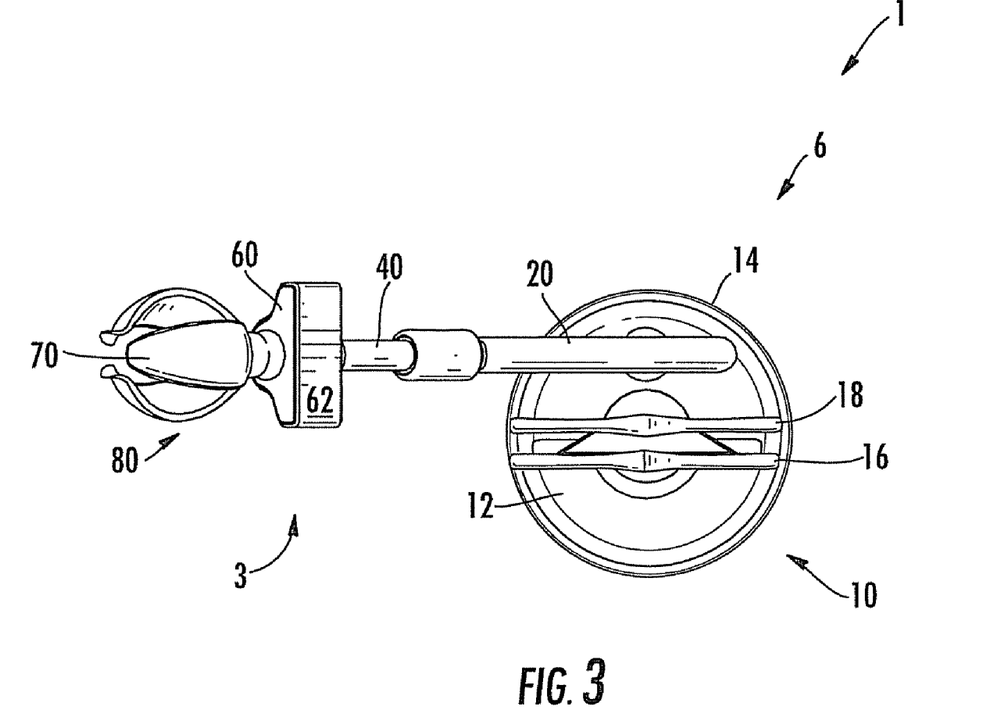
FIG. 3 is a top view of a further embodiment of a radiographic calibration apparatus in accordance with the present invention.
Figure 4:
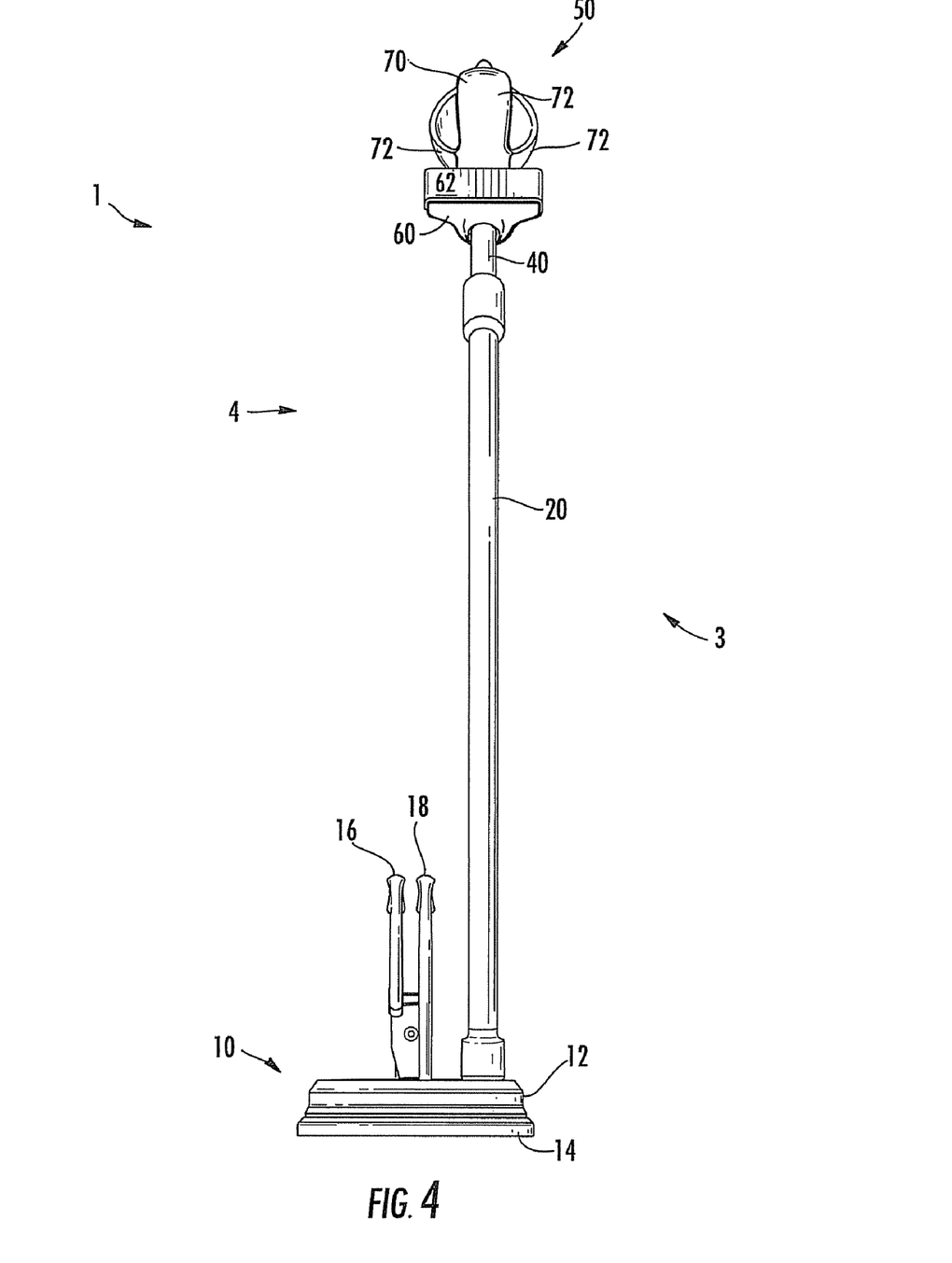
FIG. 4 is a side view of the radiographic calibration apparatus shown in FIG. 2.

FIGS. 2 and 4 illustrate another preferred and non-limiting embodiment of the present invention. A radiographic calibration apparatus ("RCA") 4 is shown having a base 10, an arm 20, and an extension 40. In FIG. 2, the RCA 4 is shown having a calibration unit retainer 50 supporting the calibration unit 90 and having a retaining member 70. Alternatively, an RCA 6 may provide that the extension 40 unitarily form a calibration unit retainer 80 that may be entirely radiolucent, as shown in FIG. 3. The extension 40 may be removably attached or affixed to the calibration unit retainer 50, as depicted in FIGS. 2 and 4-6. Further, a securing member 60 may be in operative communication with the calibration unit retainer 50, as shown in FIGS. 2-4 and 6.

As can be seen in FIGS. 2 and 4, the second end 24 of the arm 20 is in operative communication with extension 40. More specifically, the extension 40 may be releasably joined with arm 20, as shown in FIGS. 2 and 4, or may be unitarily affixed as shown in FIG. 3 (with reference to RCA 6). Accordingly, the extension 40 is in communication with and supports the calibration unit retainer 50, which is in communication with calibration unit 90. The extension 40 may be permanently affixed to calibration unit 50 or otherwise releasably engaged via threaded engagement, press fit, etc.

In addition, the extension 40 and/or calibration unit retainer 50 may integrally or removably incorporate the securing member 60. The securing member 60 may optionally have a radiopaque indicia or portion (not shown) on an outer surface 62 that will be visible in the radiographic image in order to show the size of the calibration unit 90 being employed. For example, this radiopaque indicia or portion may take the form of lead or other radiopaque material to indicate the precise dimension of the calibration unit 90 on the radiographic image. Such radiopaque indicia or portions positioned on the outer surface 62, or otherwise in relation to securing member 60, may further prevent errors made by a technologist otherwise manually transcribing the dimensions of the calibration unit 90 onto the radiographic image (e.g. x-ray image).

As can be seen in FIGS. 2-6, the retaining member 70 may be formed of a resilient material such that it may deform to receive the calibration unit 90, and thus receive the same in a supporting engagement as illustrated specifically in FIG. 2. Accordingly, the preferred and non-limiting embodiment of the calibration unit retainer 80 of FIG. 3 is a resilient unitary design, while the calibration unit retainer 50 of FIGS. 2 and 4-6 is formed in several retaining leaf portions 72. Although the calibration unit retainer 80 shown in FIG. 3 has three portions or leaves 72 forming retaining mechanism 70, the retaining member 70 may be formed as a single deformable receptacle (not shown), which effectively supports the calibration unit 90, or otherwise comprise two or more portions to engage the calibration unit 90. Further, although three leaf portions 72 are shown, it will be understood by one skilled in the art that two or more leaf portions 72 may be configured to comprise retaining member 70. Still further, a variety of shapes and deformable arrangements may be used to effectively and removably engage the calibration unit 80.

Figure 5:
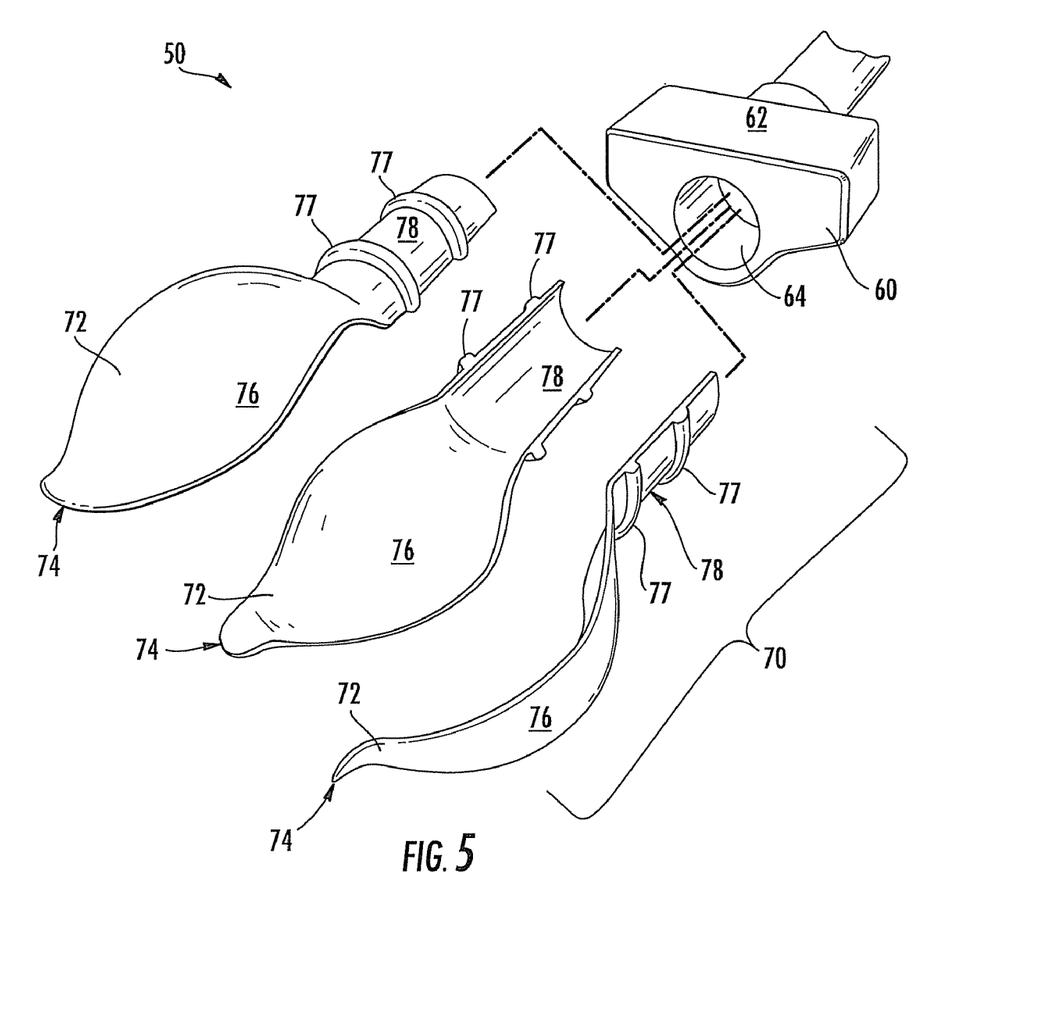
FIG. 5 is an exploded, perspective view of an embodiment of a calibration unit retainer of a radiographic calibration apparatus in accordance with the present invention.

Specifically referring to FIG. 5, and in one preferred and non-limiting embodiment, the retaining member 70 is shown disassembled in several leaf portions 72. Each leaf portion 72 has a receiving surface 74, a retaining surface 76, at least one protrusion 77 and an insertion surface 78. Accordingly, when the protrusions 77 are aligned in the illustrated embodiment in a configuration such that a somewhat unitary surface is formed about the insertion surfaces 78, the leaf portions 72 may be inserted into a bore 64 of the securing member 60. In this arrangement, the protrusions 77 releasably secure the insertion surfaces 78 inside the bore 64. Thus, when the leaf potions 72 are inserted together into the bore 64, the retaining member 70 is enabled to support the calibration unit 90. Accordingly, as mentioned previously, although three leaf portions 72 are shown, it will be understood by one skilled in the art that two or more leaf portions 72 may be configured to comprise retaining member 70.

In one embodiment, each leaf portion 72 has substantially similar surfaces 74, 76, 78 that may allow for reduced manufacturing time and/or costs relating to the retaining member 70. In addition, the receiving surfaces 74 may be configured to engage various dimensioned calibration units 90 such that the retaining member 70 may be expanded to allow the calibration unit 90 to engage or be captured by the retaining surfaces 76. Likewise, the retaining surfaces 76 may be configured to sufficiently engage and support the calibration unit 90 so as to allow for various orientations of the RCA 1.

Figure 6:
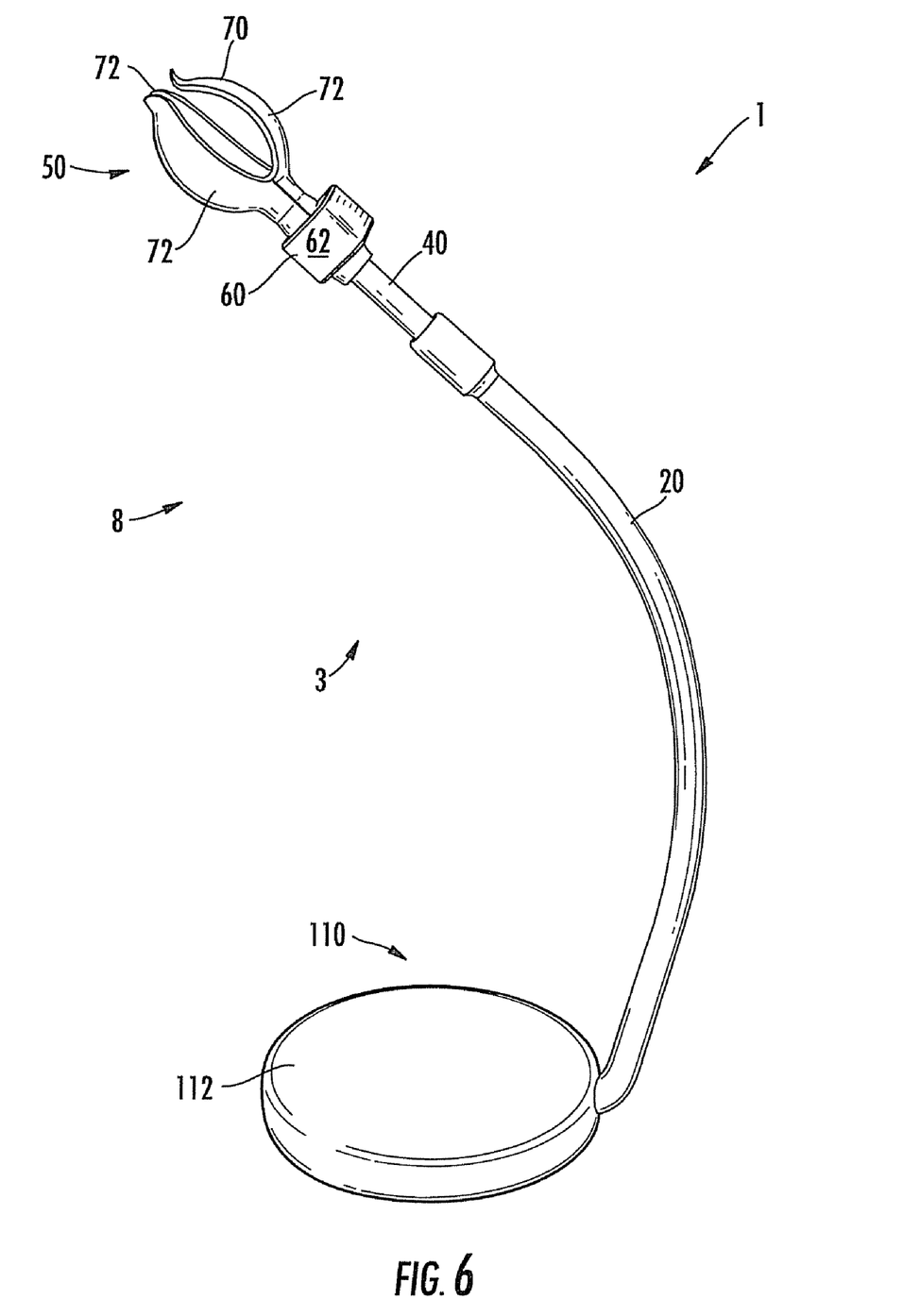
FIG. 6 is a perspective view of a still further embodiment of a radiographic calibration apparatus in accordance with the present invention.

As can be seen in a preferred and non-limiting embodiment in FIG. 6, a RCA 8 may have a base 110 that is secured to the arm 20. The RCA 8 includes an extension 40 in communication with the calibration unit retainer 50, having the securing member 60 in communication with the retaining member 70. The illustrated embodiment shows the base 110 having a disk-shaped configuration. The base 110 in this embodiment may be a pad 112, wherein the pad 112 could rest freestanding on a surface (not shown) to support the calibration unit 90 (not shown). Further, the pad 112 could be positioned in relation to a patient, such that the patient would press the pad 112 against a surface to maintain the position of the calibration unit 90 (not shown) once positioned and oriented near a radiographic target. Although the base 110 is shown in a disk-shaped configuration, other configurations may be implemented such as, for example, a bean bag configuration, flat rectangular configuration, etc. In addition, as will be understood in the art, the base 110 may have magnetic properties to secure the base 110 to ferro-metallic surfaces, adhesive properties to adhere the base 110 to surfaces, etc.

In this manner, the present invention provides a radiographic calibration unit 1 that allows for the selective positioning of a calibration unit 90 with respect to a target area of a patient. By using the novel support structure 3 described herein, the calibration unit 90 does not need to be directly affixed to the patient, such as by tape, adhesive material and the like. Instead, the present invention provides a unique arrangement and apparatus for effectively engaging in radiographic procedures using a selectively positioned and oriented calibration unit 90.

Although the invention has been described in detail for the purpose of illustration based on what is currently considered to be the most practical and preferred embodiment(s), it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. Since other modifications and changes varied to fit particular operating requirements and environments will be apparent to those skilled in the art, the invention is not considered limited to the example chosen for purposes of disclosure, and covers all changes and modifications which do not constitute departures from the spirit and scope of this invention.

The invention claimed is:

1. A radiographic calibration apparatus for supporting a calibration unit, comprising:
   a support structure configured to support and selectively position the calibration unit with respect to a patient;
   wherein the support structure comprises an extension having radiolucent properties and configured to support the calibration unit,
   wherein said extension incorporates radiopaque indicia on an outer surface thereof to indicate size of said calibration unit on a radiographic image, and
   wherein the extension is configured to be removable from the support structure.

2. The radiographic calibration apparatus of claim 1, wherein said extension is secured to the calibration unit.

3. The radiographic calibration apparatus of claim 1, wherein said extension is positioned within the outer surface of the calibration unit.

4. A radiographic calibration apparatus for supporting a calibration unit, comprising a support structure configured to support and selectively position the calibration unit with respect to a patient, wherein the support structure comprises an extension having radiolucent properties and configured to support the calibration unit, and wherein said extension further comprises a calibration unit retainer configured to at least partially surround at least a portion of the calibration unit, said calibration unit retainer having resilient properties.

5. The radiographic calibration apparatus of claim 4, wherein said calibration unit retainer further comprises a securing member secured thereto having radiopaque indicia thereon.

6. The radiographic calibration apparatus of claim 4, wherein said calibration unit retainer further comprises a retaining member configured to at least partially surround and support at least a portion of the calibration unit, said retaining member having resilient properties.

7. The radiographic calibration apparatus of claim 6, wherein said retaining member comprises at least two leaf portions configured to at least partially surround and support at least a portion of the calibration unit, said at least two leaf portions having resilient properties.

8. The radiographic calibration apparatus of claim 7, wherein each of said at least two leaf portions has a receiving surface configured to deflect said at least two leaf portions when the calibration unit is urged into contact with said receiving surface.

9. The radiographic calibration apparatus of claim 7, wherein each of said at least two leaf portions has a retaining surface configured to at least partially surround and support at least a portion of the calibration unit.

10. The radiographic calibration apparatus of claim 7, further comprising a securing member having an aperture therethrough, wherein each of said at least two leaf portions has an insertion surface having at least one radial protrusion extending therefrom and configured to secure each of said at least two leaf portions when each of said at least two leaf portions is inserted at least partially within said aperture of said securing member about said insertion surface having said at least one protrusion aligned adjacent to one another.

11. A radiographic calibration apparatus for supporting a calibration unit, comprising:
    a radiolucent extension configured to support the calibration unit;
    a repositionable arm configured to support and selectively position the radiolucent extension; and
    a base configured to support said arm and to secure said calibration unit in a desired orientation, wherein said base comprises a suction cup configured to be removably secured to a surface;
    wherein the suction cup is configured to be secured by a lever.

12. The radiographic calibration apparatus of claim 11, wherein said arm is flexible.

13. The radiographic calibration apparatus of claim 11, wherein said base further comprises a pad configured to be manually secured by a user.

14. The radiographic calibration apparatus of claim 11, wherein said extension further comprises a resilient calibration unit retainer configured to deflect and surround at least a portion of the calibration unit.

15. The radiographic calibration apparatus of claim 14, wherein said calibration unit retainer comprising:
    at least two leaf portions configured to at least partially surround and support at least a portion of the calibration unit, said at least two leaf portions having resilient properties,
    wherein each of said at least two leaf portions has a receiving surface configured to deflect said at least two leaf portions when the calibration unit is urged into contact with said receiving surface, and
    wherein each of said at least two leaf portions has a retaining surface configured to at least partially surround and support at least a portion of the calibration unit.

16. The radiographic calibration apparatus of claim 15, further comprising a securing member having an aperture therethrough, wherein each of said at least two leaf portions has an insertion surface having at least one radial protrusion extending therefrom and configured to secure each of said at least two leaf portions when each of said at least two leaf portions is at least partially inserted within said aperture of said securing member about said insertion surface having said at least one protrusion aligned adjacent to one another.

17. The radiographic calibration apparatus of claim 15, wherein said at least two leaf portions comprises three leaf portions configured substantially similarly to one another.

* * * * *